United States Patent [19]

Oh-Kita et al.

[11] Patent Number: 4,804,778

[45] Date of Patent: Feb. 14, 1989

[54] PROCESS FOR PRODUCING METHACRYLIC ACID

[75] Inventors: Motomu Oh-Kita; Kazuhiro Ishii; Masaaki Kato, all of Hiroshima, Japan

[73] Assignee: Mitsubishi Rayon Company, Ltd., Tokyo, Japan

[21] Appl. No.: 105,041

[22] Filed: Oct. 6, 1987

[30] Foreign Application Priority Data

Oct. 27, 1986 [JP] Japan .................................. 61-255402

[51] Int. Cl.$^4$ .................... C07C 57/055; C07C 51/25; C07C 51/305
[52] U.S. Cl. .................................. 562/534; 502/206; 502/209; 562/535
[58] Field of Search ................ 562/534, 535; 502/209, 502/206

[56] References Cited

U.S. PATENT DOCUMENTS

| | | | |
|---|---|---|---|
| 3,998,876 | 12/1976 | Kato et al. | 562/535 |
| 4,042,625 | 8/1977 | Matsuzawa et al. | 562/535 |
| 4,051,179 | 9/1977 | Sonobe et al. | |
| 4,118,419 | 10/1978 | Ishii et al. | 452/534 |
| 4,165,296 | 8/1979 | Ishii et al. | 562/545 X |
| 4,273,676 | 1/1981 | Matsumoto et al. | 562/534 |
| 4,320,227 | 3/1982 | Matsumoto et al. | 562/534 |
| 4,341,900 | 7/1982 | Ishii et al. | 562/532 |
| 4,469,810 | 9/1984 | Kato et al. | 502/209 |

FOREIGN PATENT DOCUMENTS

| | | |
|---|---|---|
| 2351687 | 12/1974 | Fed. Rep. of Germany. |
| 2608583 | 9/1976 | Fed. Rep. of Germany. |
| 3226721 | 4/1983 | Fed. Rep. of Germany. |
| 2538382 | 6/1984 | Fed. Rep. of Germany. |

*Primary Examiner*—Vivian Garner
*Attorney, Agent, or Firm*—Cushman, Darby & Cushman

[57] ABSTRACT

Disclosed is a process for producing methacrylic acid from methacrolein in high yields and at high selectivity which comprises vapor phase catalytic oxidation of methacrolein with molecular oxygen, characterized by using a catalyst represented by the formula: $P_aMo_bV_cCu_dZn_eA_fB_gC_hD_iO_j$ wherein P, Mo, V, Cu, Zn and O represent phosphorus, molybdenum, vanadium, copper, zinc and oxygen, respectively, A represents at least one element selected from the group consisting of antimony and iron, B represents at least one element selected from the group consisting of silicon, sulfur, selenium, scandium and gallium, C represents at least one element selected from the group consisting of potassium, rubidium, cesium and thallium, D represents at least one element selected from the group consisting of tungsten, magnesium, chromium, maganese, zirconium, tin, tantalum, bismuth, cerium, cadmium and boron, a–j indicate the atomic ratio of the respective elements and when b is 12, a is 0.1–3, c is 0.01–3, d is 0.01–3, e is 0.01–3, f is 0.1–5, g is 0.001–5, h is 0.01–3 and is 0–5 and j indicates the number of oxygen atoms necessary to satisfy valences of the respective elements.

6 Claims, No Drawings

PROCESS FOR PRODUCING METHACRYLIC ACID

BACKGROUND OF THE INVENTION

This invention relates to a catalyst used in production of methacrylic acid by vapor phase catalytic oxidation of methacrolein and a process for production of methacrylic acid.

Hitherto, there have been proposed processes for production of unsaturated carboxylic acids by vapor phase catalytic oxidation of unsaturated aldehydes in many patents. Most of them have aimed at production of acrylic acid from acrolein and when catalysts proposed in these patents are used for production of methacrylic acid, selectivity is small because of considerable side reactions and besides life of the catalyst is so short that the catalyst is not able to practically use.

On the other hand, a number of catalysts have been proposed for production of methacrylic acid from methacrolein. However, they suffer from the problems such as insufficient reaction results, a large deterioration of catalyst activity with time, too high reaction temperature, etc. Thus, further improvement in catalyst has been demanded for commercial use.

SUMMARY OF THE INVENTION

The object of this invention is to provide a process for production of methacrylic acid from methacrolein, especially a process for production of mtthacrylic acid using catalysts having high activity and selectivity and long life from a commercial viewpoint.

DESCRIPTION OF THE INVENTION

This invention relates to a process for production of methacrylic acid by vapor phase catalytic oxidation of methacrolein with molecular oxygen, characterized by using a catalyst represented by the formula: $P_a Mo_b V_c Cu_d Zn_e A_f B_g C_h D_i O_j$ (wherein P, Mo, V, Cu, Zn and 0 represent phosphorus, molybdenum, vanadium, copper, zinc and oxygen, respectively, A represents antimony and/or iron, B represents at least one element selected from the group consisting of silicon, sulfur, selenium, scandium and gallium, C represents at least one element selected from the group consisting of potassium, rubidium, cesium and thallium, D represents at least one element selected from the group consisting of tungsten, magnesium, chromium, manganese, zirconium, tin, tantalum, bismuth, cerium, cadmium and boron, a-j indicate atomic ratio of respective elements and when $b=12$, $a=0.1-3$, $c=0.01-3$, $d=0.01-3$, $e=0.01-3$, $f=0.1-5$, $g=0.001-5$, $h=0.01-3$ and $i=0-5$ and j indicates the number of oxygen atoms necessary to satisfy valences of respective elements). The catalyst can be represented by the above formula wherein i is 0.001-5. The catalyst can also be represented by the above formula wherein f is 0.2-3, g is 0.01-2.0 and i is 0.01-2.0 when B is sulfur, scandium or gallium. The catalyst can be represented, e. g., by the above formula wherein a is 0.5-2.5, b is 12, c is 0.05-2.0, d is 0.05-2.0, e is 0.05-2.0, f is 0.2-3.0, g is 0.01-2.0, h is 0.05-2.0 and i is 0.01-2.0.

According to the process of this invention, methacrylic acid can be produced from methacrolein in high yields and at high selectivity. Especially, high catalyst activity can be maintained for so long a period of time that industrial value of this process is very high.

Process for preparing the catalyst used in this invention need not be limited to specific one and various known processes such as evaporation to dryness, precipitation, CO-precipitation, etc. may be employed as far as no extremely uneven distribution of the components is caused.

As starting compounds used for preparation of catalysts, there may be used nitrate, carbonate, ammonium salt, halide, oxide and the like of respective elements in combination.

The catalyst used in the process of this invention is effective without using carriers, but it may be supported or diluted with inert carriers such as silica, alumina, silica.alumina, silicon carbide, etc.

In practice of this invention, concentration of methacrolein in the feed gas may be varied in a wide range, but suitably is 1-20 volume %, especially preferably 3-10 volume %.

The starting methacrolein may contain impurities such as water, saturated lower aldehydes, etc. in a small amount. These impurities have substantially no influence on the reaction.

It is economical to use air as an oxygen source, but if necessary, air enriched with pure oxygen may also be used.

Concentration of oxygen in the feed gas is specified by molar ratio to methacrolein and is 0.3-4, especially preferably 0.4-2.5.

The feed gas may be diluted with an inert gas such as nitrogen, steam, carbon dioxide gas or the like. Reaction pressure may be from normal pressure to several atms. Reaction temperature may be chosen within the range of 230-450° C. and especially preferably 250-400° C. The reaction may be carried out either with a fixed bed or a fluidized bed.

Preparation of the catalyst used in this invention and reaction using the catalyst will be illustrated by the following examples.

In the examples and comparative examples, the conversion of methacrolein and the selectivity for methacrylic acid produced are defined as follows:

Conversion of methacrolein (%) =

$$\frac{\text{Mol number of reacted methacrolein}}{\text{Mol number of fed methacrolein}} \times 100$$

Selectivity for methacrylic acid (%) =

$$\frac{\text{Mol number of produced methacrylic acid}}{\text{Mol number of reacted methacrolein}} \times 100$$

In the examples and comparative examples, "part" means "part by weight" and analysis was carried out by gas chromatography.

EXAMPLE 1

One hundred parts of ammonium paramolybdate, 3.3 parts of ammonium metavanadate and 4.8 parts of potassium nitrate were dissolved in 100 parts of pure water. To the solution was added a solution prepared by dissolving 8.2 parts of 85% phosphoric acid in 10 parts of pure water. Thereto were further added a solution prepared by dissolving 0.3 part of selenous acid in 5 parts of pure water and 6.9 parts of antimony trioxide, followed by heating to 95° C with stirring.

Then, thereto was added a solution prepared by dissolving 3.4 parts of copper nitrate and 4.2 parts of zinc nitrate in 50 parts of pure water and the mixed solution was evaporated to dryness at 100° C. with stirring.

The resulting solid was dried at 130° C. for 16 hours, then pressure molded and heat treated at 380° C. for 5 hours under flow of air. This was used as a catalyst.

Composition of the elements of the catalyst excluding oxygen (same in the following examples) was as follows: $P_{1.5}Mo_{12}V_{0.6}Cu_{0.3}Zn_{0.3}Sb_1Se_{0.05}K_1$.

This catalyst was charged in a reactor, through which was passed a mixed gas comprising 5% of methacrolein, 10% of oxygen, 30% of steam and 55% of nitrogen (volume%) at a reaction temperature of 290° C. for a contact time of 3.6 seconds. The reaction product was collected and analyzed by gas chromatography to find that the conversion of methacrolein was 88.3% and the selectivity for methacrylic acid was 87.2%.

The reaction was continued for about 1000 hours under the same conditions as above. The conversion of methacrolein was 88.2% and the selectivity for methacrylic acid was 87.2%.

EXAMPLES 2-12

Catalysts as shown in the following Table 1 were prepared in accordance with the procedure of Example 1 and reaction was carried out under the same conditions as in Example 1 using these catalysts to obtain the results as shown in the following Table 1.

TABLE 1

| Example | Compositions of catalysts (atomic ratios) | Conversion of methacrolein (%) | Selectivity for methacrylic acid (%) |
|---|---|---|---|
| 2 | $P_{1.5}Mo_{12}V_{0.5}Cu_{0.3}Zn_{0.3}Fe_{0.5}Sb_1Si_{0.1}Rb_1$ | 88.0 | 88.0 |
| 3 | $P_{1.5}Mo_{12}V_{0.5}Cu_{0.3}Zn_{0.3}Fe_{0.4}Sb_1S_{0.05}Tl_{0.8}$ | 89.0 | 86.9 |
| 4 | $P_{1.5}Mo_{12}V_{0.5}Cu_{0.3}Zn_{0.3}Fe_{0.4}Sb_{1.2}Si_{0.1}Cs_1W_{0.1}$ | 88.5 | 87.6 |
| 5 | $P_{1.2}Mo_{12}V_{0.5}Cu_{0.4}Zn_{0.3}Fe_{0.4}Sc_{0.1}Si_{0.1}K_1Mg_{0.1}$ | 88.4 | 87.1 |
| 6 | $P_1Mo_{12}V_{0.5}Cu_{0.4}Zn_{0.3}Fe_{0.4}Ga_{0.1}K_1Cr_{0.1}Mn_{0.05}$ | 89.1 | 86.3 |
| 7 | $P_1Mo_{12}V_{0.5}Cu_{0.4}Zn_{0.3}Fe_{0.4}S_{0.03}K_{0.5}Tl_{0.2}Zr_{0.2}$ | 88.7 | 86.9 |
| 8 | $P_1Mo_{12}V_{0.5}Cu_{0.4}Zn_{0.4}Fe_{0.4}Sb_{1.2}S_{0.04}K_1Sn_{0.1}$ | 88.5 | 87.5 |
| 9 | $P_1Mo_{12}V_{0.1}Cu_{0.4}Zn_{0.4}Fe_{0.4}Sb_{1.2}Si_{0.05}K_1Ta_{0.3}$ | 88.8 | 87.0 |
| 10 | $P_1Mo_{12}V_{0.5}Cu_{0.4}Zn_{0.4}Sb_1Si_{0.1}K_1Bi_{0.1}Ce_{0.1}$ | 89.0 | 86.5 |
| 11 | $P_{1.5}Mo_{12}V_{0.5}Cu_{0.4}Zn_{0.3}Sb_1Se_{0.1}K_1Cd_{0.1}Ce_{0.1}$ | 88.3 | 87.1 |
| 12 | $P_{1.5}Mo_{12}V_{0.5}Cu_{0.4}Zn_{0.3}Sb_1Ga_{0.1}K_1B_{0.5}Ce_{0.1}$ | 88.5 | 87.2 |

Comparative Examples 1 and 2

Comparative catalysts as shown in the following Table 2 were prepared in accordance with the procedure of Example 1 and reactions were carried out under the same conditions as in Example 1 using these catalysts to obtain the results as shown in Table 2.

TABLE 2

| Comparative Example | Composition of catalysts (atomic ratios) | Conversion of methacrolein (%) | Selectivity for methacrylic acid (%) |
|---|---|---|---|
| 1 | $P_{1.5}Mo_{12}V_{0.6}Cu_{0.3}K_1$ | 81.9 | 82.1 |
| 2 | $P_{1.5}Mo_{12}V_{0.6}Cu_{0.3}Sb_1K_1$ | 83.3 | 82.7 |

We claim:

1. A process for producing methacrylic acid by vapor phase catalytic oxidation of methacrolein with molecular oxygen which comprises carrying out the reaction in the presence of a catalyst represented by the formula: $P_aMo_bV_cCu_dZn_eA_fB_gC_hD_iO_j$ wherein P, Mo, V, Cu, Zn and O represent phosphorus, molybdenum, vanadium, copper, zinc and oxygen, respectively, A represents at least one element selected from the group consisting of antimony and iron, B represents at least one element selected from the group consisting of silicon, sulfur, selenium, scandium and gallium, C represents at least one element selected from the group consisting of potassium, rubidium, cesium and thallium, D represents at least one element selected from the group consisting of tungsten, magnesium, chromium, manganese, zirconium, tin, tantalum, bismuth, cerium, cadmium and boron, a–j indicate the atomic ratio of the respective elements and b is 12, a is 0.1–3, c is 0.01–3, d is 0.01–3, e is 0.01–3, f is 0.1–5, g is 0.001–5, h is 0.01–3 and i is 0–5 and j indicates the number of oxygen atoms necessary to satisfy the valences of the respective elements.

2. A process according to claim 1 wherein the catalyst is represented by the formula wherein i is 0.001–5.

3. A process according to claim 1 wherein the catalyst is represented by the formula wherein a is 0.5–2.5, b is 12, c is 0.05–2.0, d is 0.05'2.0, e is 0.05–2, f is 0.2–3, g is 0.01–2.0, h is 0.05–2.0 and i is 0.01–2.0.

4. A process according to claim 1 wherein the catalyst is represented by the formula wherein A is antimony.

5. A process according to claim 1 wherein the catalyst is represented by the formula wherein A is iron.

6. A process according to claim 1 wherein the catalyst is represented by the formula wherein B is sulfur, scandium or gallium, f is 0.2–3, g is 0.01–2.0 and i is 0.01–2.0.

* * * * *